(12) United States Patent
Beymer et al.

(10) Patent No.: US 11,294,938 B2
(45) Date of Patent: Apr. 5, 2022

(54) GENERALIZED DISTRIBUTED FRAMEWORK FOR PARALLEL SEARCH AND RETRIEVAL OF UNSTRUCTURED AND STRUCTURED PATIENT DATA ACROSS ZONES WITH HIERARCHICAL RANKING

(71) Applicant: International Business Machines Corporation, Armonk, NY (US)

(72) Inventors: David Beymer, San Jose, CA (US); Tanveer Syeda-Mahmood, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 83 days.

(21) Appl. No.: 16/238,974

(22) Filed: Jan. 3, 2019

(65) Prior Publication Data
US 2020/0218738 A1    Jul. 9, 2020

(51) Int. Cl.
| G06F 7/00 | (2006.01) |
| G06F 16/28 | (2019.01) |
| G06F 16/22 | (2019.01) |
| G16H 10/60 | (2018.01) |
| G06F 16/248 | (2019.01) |
| G06F 7/14 | (2006.01) |

(52) U.S. Cl.
CPC .............. *G06F 16/288* (2019.01); *G06F 7/14* (2013.01); *G06F 16/2246* (2019.01); *G06F 16/248* (2019.01); *G16H 10/60* (2018.01)

(58) Field of Classification Search
CPC .. G06F 19/328; G06F 21/6245; G06F 16/951; G06F 16/288; G06F 16/248; G06F 16/2246; G06F 7/14; G16H 10/60
USPC .......................... 707/736, 737, 747, 748, 776
See application file for complete search history.

(56) References Cited

U.S. PATENT DOCUMENTS

| 5,930,800 | A | 7/1999 | Hara et al. | |
| 6,128,621 | A | 10/2000 | Weisz | |
| 9,378,271 | B2 | 6/2016 | Rassen et al. | |
| 2004/0236767 | A1 | 11/2004 | Soylemez et al. | |
| 2006/0088042 | A1* | 4/2006 | Shoham | H04L 67/06 370/401 |
| 2009/0198669 | A1* | 8/2009 | Shaw | G06F 16/951 |
| 2012/0130745 | A1 | 5/2012 | Jones | |
| 2013/0271777 | A1 | 10/2013 | Ito | |
| 2014/0142984 | A1 | 5/2014 | Wright et al. | |
| 2015/0120695 | A1 | 4/2015 | Vasu et al. | |
| 2015/0127379 | A1 | 5/2015 | Sorenson | |
| 2017/0277668 | A1* | 9/2017 | Luo | G06F 16/345 |
| 2018/0091306 | A1* | 3/2018 | Antonopoulos | G06F 21/57 |
| 2019/0213407 | A1* | 7/2019 | Toivanen | G06N 7/005 |

(Continued)

*Primary Examiner* — Md I Uddin
(74) *Attorney, Agent, or Firm* — Erik A. Huestis; Stephen J. Kenny; Foley Hoag. LLC (57) ABSTRACT

A generalized distributed framework is provided for parallel search and retrieval of unstructured and structured patient data across zones with hierarchical ranking. In various embodiments, patient data is ingested from a plurality of data sources. A plurality of data models is populated based on the ingested patient data, each data model comprising an abstract data type. The plurality of data models is stored in an index. A search request is processed against the index, the search request comprising one or more attribute of the abstract data type.

17 Claims, 5 Drawing Sheets

(56) References Cited

U.S. PATENT DOCUMENTS

2020/0012741 A1\* 1/2020 Bracholdt ............. G06F 16/288
2020/0218738 A1 7/2020 Beymer et al.

\* cited by examiner

GENERALIZED DISTRIBUTED FRAMEWORK FOR PARALLEL SEARCH AND RETRIEVAL OF UNSTRUCTURED AND STRUCTURED PATIENT DATA ACROSS ZONES WITH HIERARCHICAL RANKING

BACKGROUND

Embodiments of the present disclosure relate to search and retrieval of patient data, and more specifically, to a generalized distributed framework for parallel search and retrieval of unstructured and structured patient data across zones with hierarchical ranking.

BRIEF SUMMARY

According to embodiments of the present disclosure, methods of and computer program products for modeling patient data are provided. In various embodiments, patient data is ingested from a plurality of data sources. A plurality of data models is populated based on the ingested patient data, each data model comprising an abstract data type. The plurality of data models is stored in an index. A search request is processed against the index, the search request comprising one or more attribute of the abstract data type.

DETAILED DESCRIPTION

Patient data may be spread across a large variety of systems, and may be stored in structured or unstructured form. There is a need for a distributed framework suitable for search and retrieval across such data sources. To address this and other needs, a generalized distributed framework for parallel search and retrieval of unstructured and structured patient data across zones with hierarchical ranking is provided leveraging abstract data types (ADT) in general.

In various embodiments, analytics longitudinal patient records are provided. These comprise a collection of time-varying multimodal structured and unstructured information that represents the longitudinal clinical history of the patient as needed for analytical processing. Overlapping content is provided, with various different views of the information. In this way, patient information is collected and represented by abstracting out the patient details in terms of comparative effectiveness research variables, including demographics, diagnosis, medications, signs and symptoms, procedures, etc. These details may be modeled as time-varying functions.

Figure 1:
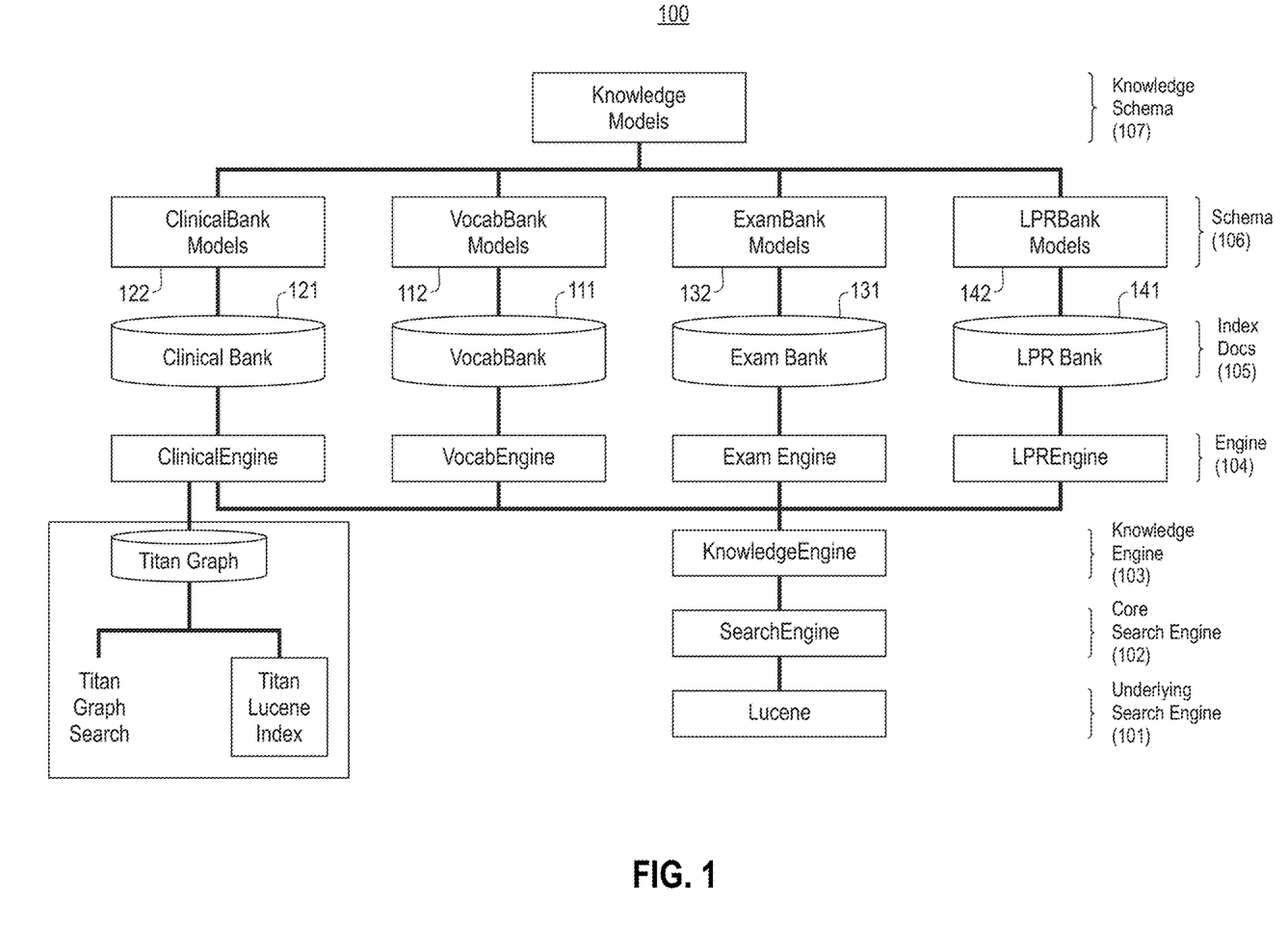
FIG. 1 illustrates a system for management of abstract data types according to embodiments of the present disclosure.

With reference now to FIG. 1, a system for management of abstract data types is illustrated according to embodiments of the present disclosure. In general system 100 is organized into four levels: underlying search engine 101 (which in some embodiments may be Lucene); core search engine 102 (to support management of abstract models derived from knowledge of different kinds, such as patient-specific knowledge or clinical knowledge); knowledge engine 103 (dealing specifically with knowledge-related operations); and bank search engines 104 (which are specific to the types of knowledge modeled, such as patient-specific knowledge or clinical knowledge).

The information to be modeled is represented programmatically through abstract data types and stored in the banks as indexed documents 105, which shred the abstract data type elements according to their data types, conforming to corresponding schemas 106 in corresponding data models. In addition, knowledge schema 107 corresponds to an overall knowledge model. By storing and searching data models, various advantages are realized. Powerful querying is possible because structured objects can be directly queried by population of relevant fields. Relative order can be preserved during querying (e.g., array order). Unlike relational schemas in databases, the ADT can be changed after design and easily updated.

An abstract model captures essential elements needed for all data models in a given application. In the present example, the models LPRKnowledgeModel, VocabModel, and ClinicalKnowledgeModel are domain-specific subclasses. The knowledge model captures generic elements of features derived from any knowledge objects. For example, a GenericFeature model may capture provenance, scoring, and valuetypes.

While the knowledge model may be used to abstractly describe many kinds of knowledge such as clinical knowledge, exam knowledge, or analytics knowledge, various examples described herein focus on patient-specific knowledge. This patient-specific knowledge is modeled as a bank known as ALPR Bank, which stands for analytics-geared longitudinal patient record (ALPR).

ALPRBank 141 is an abstract model used to model many elements of the patient record has associated patient-specific data models. The base classes for ALPR are ALPRKnowledgeModel and AalimDataModel. In some embodiments, ALPRBank stores 21 models, modeling different aspects of a patient's clinical record that are important for enabling clinical informatics: Person, PatientDemographics, PatientAnatomy, PatientDiagnosis, PatientDrugs, PatientEncounter, PatientExamData, PatientFeature, PatientHistory, PatientInfo, PatientMeasurements, PatientMedia, PatientMediaRun, PatientOutcome, PatientRiskFactors, PatientStudy, PatientSymptoms, PatientTreatment, PatientVisit, PatientVitals, and OrgInfoModel. Additional models are helper classes for the stored models: AddressModel and ScoreModel. The bank also houses models needed for speed lookup of content across distributed repositories. These keep track of organizations, patients, their studies, exams, and other associated data. Context models are provided to capture LPR repository structure for display of LPR (not stored in index): Person, PatientDemographics, PatientAnatomy, PatientDiagnosis, PatientDrugs, PatientEncounter, PatientExamData, PatientFeature, PatientHistory, PatientInfo, PatientMeasurements, PatientMedia, PatientMediaRun, PatientOutcome, PatientRiskFactors, PatientStudy, PatientSymptoms, PatientTreatment, PatientVisit, PatientVitals, and OrgInfoModel.

Each storable data model is stored as a single document. Each data model has fields ($f_1, f_2, \ldots, f_n$). Each data model can have primary keys, search keys, grouping keys, and untokenized keys. Primary keys are similar to primary key in a relational table, for example, providing a unique ID or set of IDs to designate a row or a document uniquely. Search keys are similar to logical primary keys in a relational table. Grouping keys are used for skimming in search. In some embodiments, Lucene keeps track of them through special collectors. Untokenized keys tell the lowest level search engine document formation step to preserve certain fields without tokenization. This field is useful for enumerated types. In various embodiments, the above information is stored as Java annotations.

The ADT representation in a document is as follows. The original data model may be represented as a set of name-value pairs ADT=$\{<f_1,v_1>,<f_2,v_2>, \ldots <f_n,v_n>\}$. Only one copy of the same name-value pair is indexed. A created document may be represented as D=$<F_g,F_p,F_u,F_i,m,u,S>$.

A grouping key may be represented as $F_g=\{<f_g,v_g>\}$, $|F_g|=1$. An untokenized key may be represented as $F_u=\{<f_u, v_u>,<f_u\cdot fsn,v_u>\}, |F_u| \geq 0$. A primary key may be represented as $F_P=\{<f_p\cdot ORG, v_p>\}, |F_p| \geq 1$.

$F_i=\{H_i\}, |F_i| \geq 1$, where $$H_i = \begin{cases} K(f_i) \text{ if } f_i \text{ is atomic} \\ <\{K(l_j)\}, <f_i \cdot \text{length}, |f_i| >> \forall l_j \in f_i, \end{cases}$$

if $f_i$ is an array and $K(f_i)=\{K^o(f_i), K^{fsn}(f_i), K^{fieldname}(f_i), K^t(f_i), K^n(f_i), K^d(f_i)\}$. Given the original field-value pairs, $K^o(f_i)=<f_i,v_i>$. Normalized value may be represented as $K^{fsn}(f_i)=<f_i\cdot fsn, N(v_i)>$, $N(v_i)$. Tokenized value may be represented as $K^t(f_i)=\{<f_i,v_{ti}>\}$, $v_{ti}$ is a term of $v_i$. For fieldname="field-value", $K^{fieldname}(f_i)=<\text{fieldname}, "f_i=v_i">$. For number terms as numeric fields, $K^n(f_i)=\{<f_i, v_{ni}>\}$, $v_{ni}$ is a numeric term of $v_i$. For date terms as date fields, $K^d(f_i)=\{<f_i,v_{di}>\}$, $v_{di}$ is a date term of $v_i$.

$$m = <modelname = \text{Name}(ADT)>.$$

$$u = <\text{Name}(ADT) \cdot updateStatus = \begin{cases} NO\_DELETE \\ SOFT\_DELETE> . \\ HARD\_DELETE \end{cases}$$

$$S = <serialized\_obj = \text{Serialized}(ADT)>.$$

Adopting the above example, consider the multiple field types provided below in Inset 1.

---
Inset 1
---
ConceptModel.name ="Hello World"
ConceptModel.score=2.0
ConceptModel.date="10-21-2014"
ConceptModel.ontology[0].conceptname="Foo Baz 223 10-22-2014"
---

The field value pairs indexed are then provided in Inset 2-Inset 5.

---
Inset 2
---
ConceptModel.name="Hello World"
ConceptModel.name.fsn="hello world"
fieldname="ConceptModel.name=Hello World"
ConceptModel.name="hello"
ConceptModel.name="world"
---

---
Inset 3
---
ConceptModel.score=2.0
ConceptModel.score.fsn=2.0
fieldname="ConceptModel.score=2.0"
ConceptModel.score="2.0"
---

---
Inset 4
---
ConceptModel.date="10-21-2014"
ConceptModel.date.fsn="10-21-2014"
fieldname="ConceptModel.date=10-21-2014"
ConceptModel.date="20141021093211"
---

---
Inset 5
---
Fieldname="ConceptModel.ontology.length=1"
ConceptModel.ontology.conceptname="Foo Baz 223 10-22-2014"
ConceptModel.ontology.conceptname.fsn="foo baz 223 10-22-2014"
fieldname="ConceptModel.ontology.conceptname="Foo Baz 10-22-2014"
ConceptModel.ontology.conceptname="foo"
ConceptModel.ontology.conceptname="baz"
ConceptModel.ontology.conceptname="223"
ConceptModel.ontology.conceptname=223.0
ConceptModel.ontology.conceptname="10-22-2014"
Conceptmodel.ontology.conceptname="20141022093224"
---

As noted above, various operation on documents are provided according to embodiments of this disclosure. These may include inserts, updates, deletes, search, skim, sharding, and batch operations.

Considering index operations on a single index, including inserts, updates, and deletes, the input is a data model derived from KnowledgeModel. The output is a new document corresponding to the data model in the index. To check if a document already exists in the index, the search keys or the primary key may be used if a specific document is desired. Besides retrieval of existing documents, other operation may include a HARD_DELETE, deleting the document from the index, a SOFT_DELETE updating the retrieved model with a status of SOFT_DELETE, or UPDATE, merging the current model with the retrieved model.

Adding a new document may include extraction of all fields of the knowledge model, including inherited fields, creating an initial document with the fields, enhancing the document, drop the document from the index if it exists, and insert the new document.

Search operations on a single index may include various options. For example, search options may be based on input types, including Boolean Queries (when one wants to be specific and knows field names) or Partially filled data models. In some embodiments, automatic query expansion is provided by tokenization of fields. Various search methods are provided, including skimming (counting how many matches are there), generic search (searching for unknown models=>multiple models returned), and retrieve (searching for known model=>resulting model is unique). Various desired outputs are available, including fully populated data models, documents grouped by search keys (more details on documents, allows for re-ranking post-search), and ranked document ID lists (for quick pruning). In some embodiments, each document has a search engine ranking score, such as those provided by Lucene, and numhits for separate scoring. While search engines alone may store and retrieve document, the current disclosure provides a layer on top of search engines to achieve the goals of patient data management and accurate retrieval of patient records from even imprecise specification of queries based on partial knowledge of the patient's record. One such example is query expansion, explained below.

In various embodiments, query expansion is provided. When queries are partial data models, all active fields are extracted (e.g., non-null or non-initialized). Each field type is inspected and an appropriate Boolean query is formulated. Strings get tokenized, phrase-ordered with slop in addition to their original form. Numbers get formulated as both strings, and numeric query ranges. Dates get formulated as strings and dates in both time formats (UTC and string form). UUID and other untokenized types are retained as is. In various embodiments, further customization is provided in respective bank search engines. For example, synonym expansion or ontological expansion may be provided using the companion clinical knowledge housed in the Clincal-Bank, which is also implemented as a subclass of the more general KnowledgeModel.

When indexes grow larger than about 100 GB, custom sharding may be necessary. In various embodiments, all data about a given entity is located in the same shard (e.g., for a given patient). Batch inserts and deletes are desirable in various implementations, which requires grouping all documents belonging to a single patient. In addition, various embodiments provide parallel search of shards through independent index searchers.

For batch insert, update, or deletes with sharding, the input is a list of data models to be inserted, updated, or deleted. The output is updated documents in the index. For each model, the shard it belongs to and its size are identified. A Boolean query may be created for the model. All models with hits are grouped in their respective shards and updated models are retrieved after merging and enhancing. A large Boolean query is formed per shard of all the models in the shard. The old documents are batch deleted. The new documents are batch inserted.

To provide search with sharding, all searchers for index shards are collected. Matching shards are found per query. Shards are searched separately (which can be parallelized). The results returned are merged.

It will be appreciated that the system described above is useful in a variety of environments for a variety of data types. For example, all organizations in the LPRBank can be found by making an empty OrgInfoModel and passing it to generic search. In another example, all concepts which are ontologically related by two levels of depth in between can be found by constructing a ConceptModel with an ontology element of distance=2.

Figure 2:
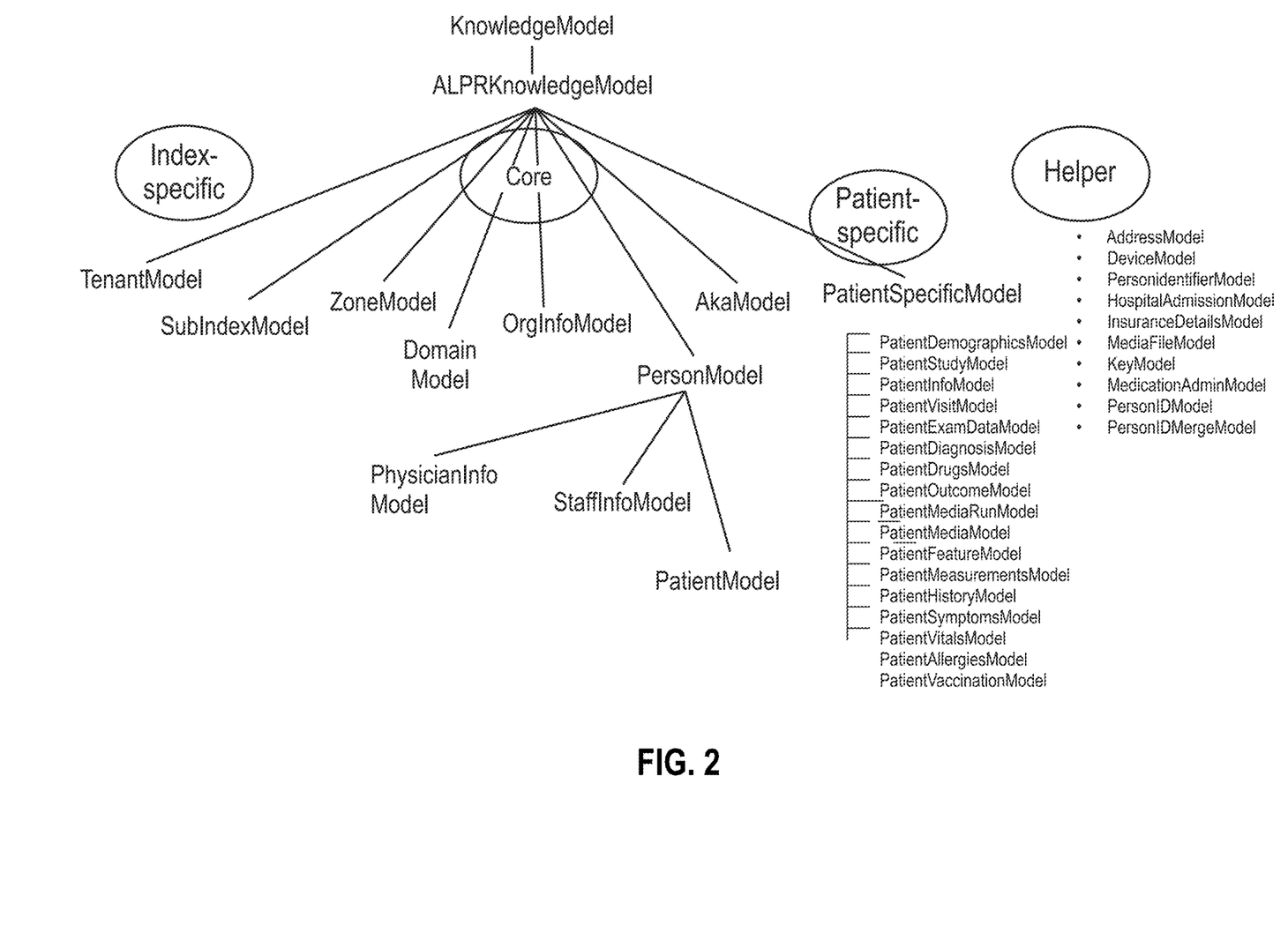
FIG. 2 illustrates an exemplary logical models hierarchy according to embodiments of the present disclosure.

Referring to FIG. 2, an exemplary Logical Models Hierarchy is illustrated according to embodiments of the present disclosure. This model hierarchy accommodates Core models, including Entities such as Organizations, zones, and domains, Person entities such as Physicians, Staff, and Patients, and Person ID management-related entities, such as Person, and a/k/a. The hierarchy also accommodates Helper models, including Person identifiers, Addresses, Devices, Media details, Hospital admissions, insurances, or Medication administration. The hierarchy also accommodates Index management, including Tenants, or TOC models for Tenants, Zones, Patients, Studies, Exams, MediaRun, or Media. The hierarchy also accommodates Patient-specific models, including Demographics, Studies, Visits, Exams, Symptoms, Diagnosis, Medications, Measurements, Vitals, Allergies, Vaccinations, Features, MediaRun, Media, Treatments, or Outcome.

In various embodiments, the information extracted from the raw patient data modeled in the above LPR models is further represented as a clinical feature model that provides links to knowledge concepts. In this way, structured and unstructured results and their interpreters are handled. This approach is applicable to other knowledge models besides patient knowledge. For example, this approach is applicable to Measurements extracted from imaging, Measurements extracted from reports, Diagnosis, problems, symptoms, medications, or family history automatically extracted from reports, Similar patient lists, Differential diagnosis list, Learned models per image, LBP, SIFT, HOG, or Motion maps.

In various embodiments, a ClinicalFeatureModel may be associated with any of the ALPR models, including PatientMeasurementsModel (holds any structured measurements from external sources), PatientDiagnosisModel (any feature that is of concept type diagnosis), PatientSymptomsModel (any feature that is of concept type symptoms), PatientOutcomeModel, PatientTreatmentModel, PatientExamDataModel, PatientDemographicsModel, PatientDrugsModel, PatientVitalsModel, PatientAllergiesModel, PatientVaccinationModel, or PatientFeatureModel (Catch all for all other features that don't belong to any of the types above). In various embodiments, each analytic knows which models to populate in the current analytics pipelines.

In an exemplary embodiment, the clinical feature model may be parametrized as set forth below in Inset 6 to Inset 10.

| Inset 6 |
| --- |
| ClinicalFeatureModel<br>    KnowledgeModel conceptype;<br>    ClinicalFeatureModel[ ] children; –> Allows recursive specification<br>        String relationtype;<br>    String name;<br>    FeatureMetadataModel metadata;<br>    FeatureContentModel content;<br>    ProvenanceModel provenance; |

| Inset 7 |
| --- |
| FeatureMetadataModel<br>    String description;<br>    KeyModel algorithm;<br>    Double prob;<br>        Double conf;<br>    Double relevance;<br>    Double weight;<br>    Modality modality;<br>    Specialty specialty;<br>    Boolean negation;<br>    Boolean automatic; |

| Inset 8 |
| --- |
| FeatureContentModel<br>    ValueType value;<br>    KeyModel featureReader;<br>    String location;<br>    Boolean direct; |

---
Inset 9
---
ProvenanceModel -> Frequently subclassed by analytics to capture more details. Hence needs typecasting support for non-object-oriented architectures
    String description;
    ProvenanceSourceType provenanceSource;
    Date refDate;
    private String[ ] refURLs;
---

---
Inset 10
---
ValueType
    Object value;
    String unit;
    String group;
    String valueRange;
    String rangeSemantics;
    String label;
    KeyModel conceptType;
---

An exemplary patient feature model is described in Inset 11. This provides a generic representation to handle results of any analytics. It allows for descriptions of analytics, as well as their results, allows visualizations to be specified with the features, and allows multiple features to be associated with a patient data.

---
Inset 11
---
PatientFeatureModel
private VisualizationType vistype;   private String featurename;
    KeyModel mediaID; //PatientMediaModel
    KeyModel runID; //PatientMediaRunModel
    KeyModel examID; //PatientExamDataModel
    eyModel studyID; //PatientStudyModel
    // KeyModel patientID;
    private String featureSrcPath;//for copying over the unstructured files
    private String featureURL;
    String featureExtID;//some external way to refer to feature frequently by its name
    Date recordedDate;
    ClinicalFeatureModel[ ] featuredesc; //description of features associated with the model
---

Figure 3:
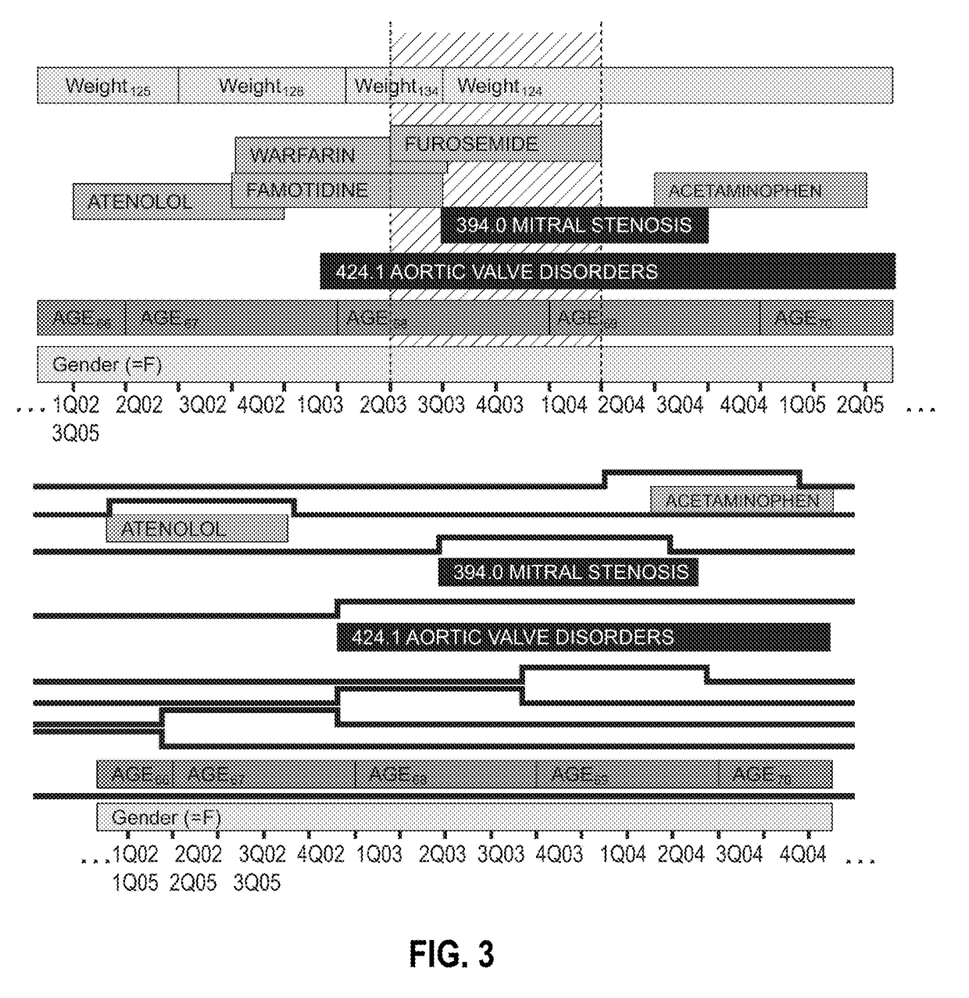
FIG. 3 illustrates an exemplary arrangement of multiple patient features according to embodiments of the present disclosure.

Referring to FIG. 3, an exemplary arrangement of multiple patient features is provided. In this exemplary visualization, a plurality of patient-specific knowledge from multiple sources is organized in a manner that is conducive to inference.

In various embodiments, patient-specific knowledge is captured through a data model that models a Patient's longitudinal clinical history, Admission and administration information regarding patients, Derived clinical features from analytical processing of patient data, and Metadata about unstructured patient data. This patient information is represented through structured data model captured as searchable documents. Documents are customized to allow fast search with skimming for information at the patient level. The information modeled in this representation are discrete elements. Blobs are not stored in the data model, instead a pointer is made to the repository storage. This reduces the size requirements of the database.

Raw patient data are captured in a patient repository. Repository structure is used to capture unstructured information. While pointers can be put in an object-based storage, having it organized in a hierarchy helps in image analytics operations without having to consult the database frequently.

In various embodiments, data is stored in mirrored organizational repositories, including an Original (temporary) repository, an analytic repository, and a Visualization (application) repository. The Original repository contains the patient data as captured from the parent organization (Customer-data). The original data includes DICOM, textual reports, EKG traces, etc. This store is temporary until the analytical processing is completed. The information in the Analytic repository is derived from the original data and organized at the relevant level of patient data.

In various embodiments, a patient's longitudinal clinical history includes Demographics, EMPI/PHI factors, Risk factors, History and Physical (e.g., Family, social), Vitals signs, Allergies and immunizations, Medications & prescriptions (e.g., Prescribed, taken), Encounters, visits and orders (e.g., Chief complaint), Diagnostic, screening studies, Labs, Diagnosis (e.g., Working, admitting, principal, secondary, confirmed, billed diagnosis), Significant problems (e.g., Problem lists), Symptoms, risks, prognosis, contraindications, Procedures, Treatments and patient management, Outcomes data, Imaging (e.g., Diagnostic, Screening Exams, Modalities used in exams, Modality runs, Images within runs), Reports (e.g., Diagnostic reports including pathology, cardiology, etc., Clinical history notes, admission, discharge summaries), Extracted measurements (e.g., from Labs, analysis of reports, imaging, etc.).

In various embodiments a patient's associated information includes, Hospital admissions, visits, and encounters, Physicians, Staff, Researchers, Patients, Facilities & organizations, Insurance details, claims and payments, Instruments and usage, Examination types, Countries and state-specific details.

In various embodiments, Derived clinical features include Structured and unstructured features (Linked back to patients, studies, exams, runs, images, etc.), Visualizations of features, Semantic description of features (Using clinical knowledge concepts and relations), Feature metadata (Manual or automatic, algorithms, probability, relevance, modality, specialty, etc.), Feature content (Formats, readers, location details, feature blobs, values), Feature provenance (Source type, matching details (text, image, ROI), etc.).

In various embodiments, analytics-geared longitudinal patient record (ALPR) ingestion is provided. The models described herein are populated from incoming data. Data may be drawn from custom adapters, HL7 ingestion, DICOM ingestion, or Patient ID Merge.

As part of the ingestion process, cross-references among models are filled-up, including filling-up foreign key references and cross-references to clinical knowledge and concepts. With respect to unstructured data, models are inserted updated, or deleted as needed.

In various embodiments, the ALPR models are populated in-memory. Cross-referencing is then performed with common models followed by patient-specific models in the correct order. ALPR models are populated in the order given, filling up foreign key references using search keys. When a key is a foreign key, a KeyModel is created and filled-in with as many of the skeys as possible from the current ingestion steps. The pkey remains blank as it is not known at this point.

In various embodiments, models are cross-referenced by searching for the models in an order specified using an insert/update rule. If the search keys are partially specified, this step is handled as an update using the insert/update rule. The rest of the KeyModel is filled-in in the HashMap for use later. The foreign keys are filled-in in the model using the looked up KeyModel in the HashMap. The above is repeated for all models in order with common models going ahead of patient-specific models.

In an exemplary patient lookup, a query is received referring to a patient by one or more attributes in the PersonIdentifierModel (e.g. tenantExtID, MRN). The PersonModel is recovered. All the variants are recovered from the AkaModel. The query is automatically expanded to retrieve all requested models under all ids of the patient. They are then resolved back into a reference ID based on the original query. The results are then returned to the application.

In various embodiments, a foreign key is designated both through reference to its primary key and search keys. The Foreign Key is handled as a KeyModel. In an exemplary embodiments, a KeyModel comprises an internal id of the model as the primary key; the search keys that serve as virtual primary keys; an model name to remember the model whose ID is being captured; a description serving as a string placeholder until search keys can be determined, all keys that can be exported to applications, a location for those models with unstructured files. The advantage of bundling all references under a key model is that any model can be searched in one step even when the primary keys are unknown through one of these attributes. In most applications primary keys are unknown and are retrieved after search. Search keys for the KeyModel can be generated through an iterative walkthrough of the dependent models.

In contrast, using a single string to represent a foreign key may cause search to erroneously retrieve the wrong foreign key when searched by a single string. If the search string were from primary key, it would be suitable for retrieving the desired result, but this key is usually not known. KeyModel generation is automatic so no extra effort in specifying it over a simple string foreign key.

In various embodiments, information is stored in each document per model. These include a serialized object for fast recovery; Update status about the model (inserted, updated, soft delete, hard delete); Name of the model (helps in consolidating all models of the same type for counting purpose); A single grouping key (for search skimming); and A primary key. All fields that are not to be tokenized go as is in two forms. All fields that are tokenized are subanalyzed, by Separating the terms, Recognizing if a term is a number, and Recognizing if a term is a date. All tokenized fields have multiple forms: Original field value pair; Normalized value pair; Every token assigned to the same field name; Every token that is a number assigned to the field as a range value; Every token that is a date assigned to the field as a date value; A new field created with the name=fieldname and value=field,value pair.

During model insert, a tokenization process during model insertion enhances the model document to enable robust searching. Since each unstructured data element is associated with a structured model, the hint for creation of repository structure is provided. As the structured data gets inserted/updated, if these models are associated with an unstructured content, then the corresponding organizational repositories are automatically created using a naming system specified in the TOC models.

Structured models may result in a file repository structure. For example, PatientStudyModel may be used for studies associated with exams and procedures that either have imaging, time series, or reports (genomic and other data in future), PatientExamDataModel may be used for exams and procedures that have imaging, time series, or reports (genomic and other data in future). Correspondence between models and their associated file content is retained through pointers in the model. Clinical feature models can represent fairly complex analytics results.

In various embodiments, a Lookup is provided by primary key, and is intended to retrieve the unique model by primary key. Search is provided by search key or other keys, and can lead to multiple models.

Searching for a model may be performed by Search keys (one or more) or other fields. Possible search results includes that no model exists, in which case the model is inserted, exactly one model exists, in which case the model is updated using update rule, or more than one model exists, in which case the update rule is applied to all the models with the highest matching rank.

In updating, since the model exists in this case, the primary key is used to retrieve the model. A new model is produced that is a merger of the old model and the new model. The existing model is deleted. The new model is inserted. To find the highest matching rank models, the retrieved models are ranked to pick those models that have the largest number of search keys match to those specified in the query. According to a first merge rule, (assumes all models are sent in the correct order during ingestion), all those fields in the old model whose values in the current model are null are retained, all other fields are replaced with those in the new model. According to a second merge rule, all fields of the old model are replaced with the new model. So if some of the new model fields are null, they will overwrite the old field value. According to a third merge rule, (If order of arrival cannot be guaranteed) all KnowledgeModels have a date field. The first merge rule is applied if current model is of a more recent date, else the order of the models to be merged is reversed (e.g., Merge old into new rather than new into old).

In various embodiments, search may be provided in several ways. A desired model may be populated as much as one knows, and all models that satisfy those criteria are retrieved. A specific model may be retrieved by its primary key. A custom query may be constructed to retrieve exactly what you need from one model type. Join may be provided across models for search. Search can be specified to be exact or approximate. Re-ranking is performed for distributed search using a match to the attributes both in number and extent (for partially specified models). Search and access may be supported through a small set of APIs. Search may be achieved through a common API for accessing abstract data types of KnowledgeModel class. In various embodiments, a common search engine is leveraged across all banks.

Figure 4:
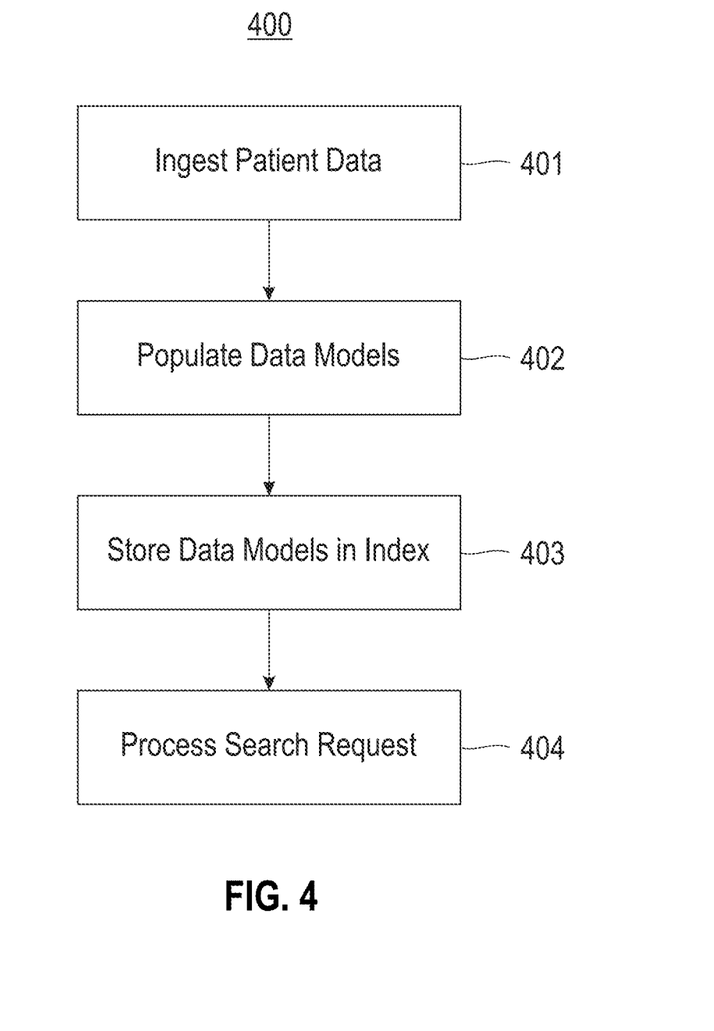
FIG. 4 illustrates a method of modeling patient data according to embodiments of the present disclosure.

Referring to FIG. 4, a method of modeling patient data is illustrated according to embodiments of the present disclosure. At 401, patient data is ingested from a plurality of data sources. At 402, a plurality of data models is populated based on the ingested patient data, each data model comprising an abstract data type. At 403, the plurality of data models is stored in an index. At 404, a search request is processed against the index, the search request comprising one or more attribute of the abstract data type.

It will be appreciated from the above description that the present disclosure provides for the distribution of patient record management functions. Ingest, search, are update functions are provided. Flexible querying is enabled while still maintaining the precision of database retrieval. The data models are provided for capturing essential clinical information about a patient. Efficient representation and search complexity are provided for handling distributed repositories.

Figure 5:
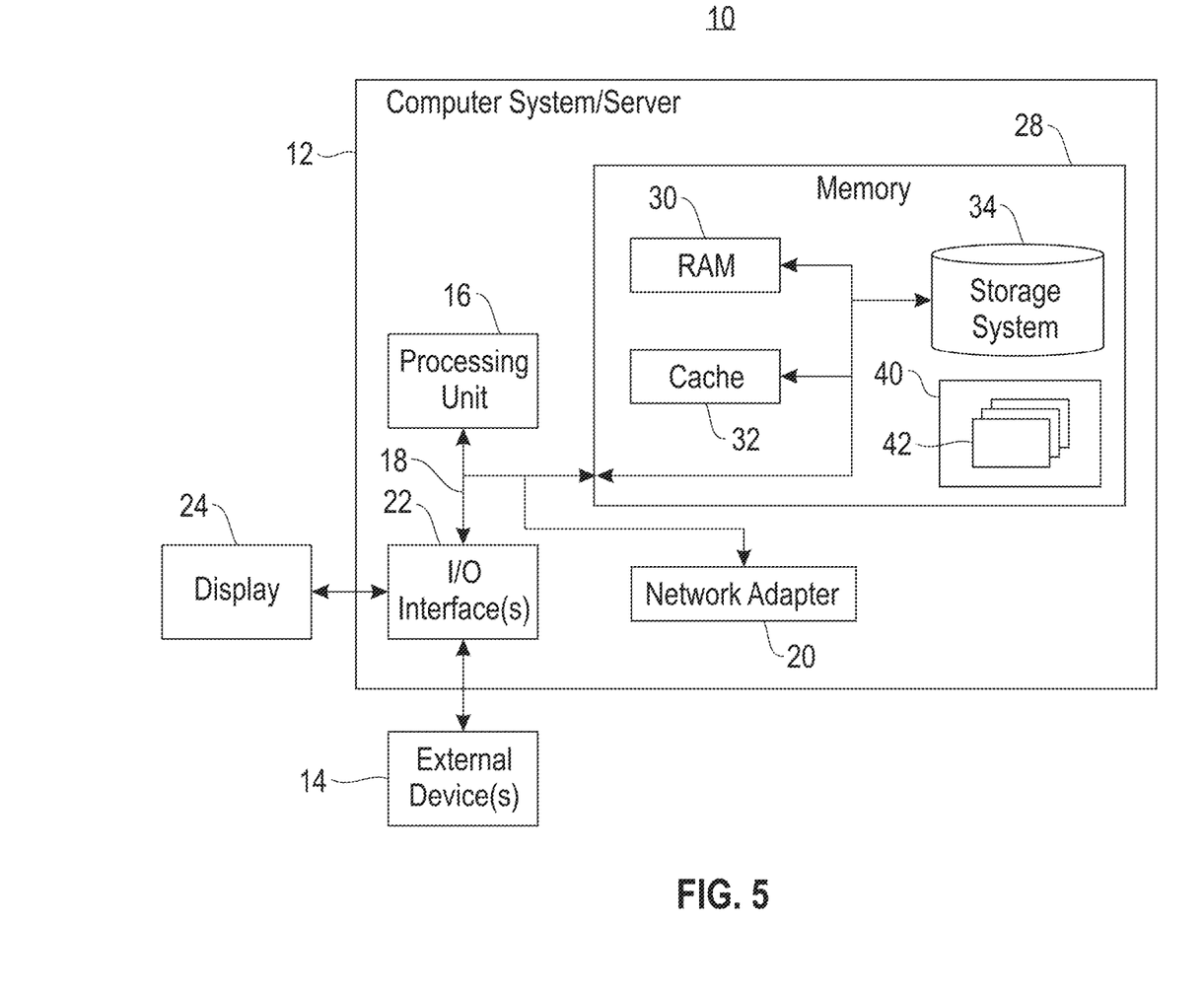
FIG. 5 depicts a computing node according to an embodiment of the present disclosure.

Referring now to FIG. 5, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   ingesting a collection of structured and unstructured patient data, the patient data comprising a plurality of modalities, the patient data comprising a longitudinal clinical history of one or more patients, the patient data from a plurality of data sources;
   populating a plurality of data models based on the ingested patient data to provide for parallel search, retrieval, and hierarchical ranking of the patient data from the plurality of data sources, each data model comprising an abstract data type having a primary key configured to uniquely designate a row or a document, a search key configured to separately designate a row or a document, a grouping key configured to count number of matches to a query, and an untokenized key configured to preserve one or more predetermined fields of the document definition without tokenization, wherein the plurality of data models comprise one or more domain-specific subclasses;

storing the plurality of data models as one or more indexed documents in an index, each data model being associated with one or more schemas, each data model representing patient data according to one or more data types within the respective patient data, and each data model conforming to at least one of the one or more schemas;

processing a search request against the index, the search request comprising one or more attribute of the abstract data type, wherein the search request is automatically expanded to retrieve one or more of the plurality of data models based on one or more additional attributes associated with the one or more attribute; and providing a search result by collecting one or more shards based on the search request.

2. The method of claim 1, further comprising outputting a result of the search request.

3. The method of claim 2, wherein the output of the search request is sorted based on quality of match.

4. The method of claim 1, wherein populating the plurality of data models comprises generating and merging a data model for ingested patient data.

5. The method of claim 1, further comprising:
outputting the data models in a time series.

6. The method of claim 1, the abstract data type reflecting a class hierarchy.

7. A system comprising:
a computing node comprising a computer readable storage medium having program instructions embodied therewith, the program instructions executable by a processor of the computing node to cause the processor to perform a method comprising:
ingesting a collection of structured and unstructured patient data, the patient data comprising a plurality of modalities, the patient data comprising a longitudinal clinical history of one or more patients, the patient data from a plurality of data sources;
populating a plurality of data models based on the ingested patient data to provide for parallel search, retrieval, and hierarchical ranking of the patient data from the plurality of data sources, each data model comprising an abstract data type having a primary key configured to uniquely designate a row or a document, a search key configured to separately designate a row or a document, a grouping key configured to count number of matches to a query, and an untokenized key configured to preserve one or more predetermined fields of the document definition without tokenization, wherein the plurality of data models comprise one or more domain-specific subclasses;
storing the plurality of data models as one or more indexed documents in an index, each data model being associated with one or more schemas, each data model representing patient data according to one or more data types within the respective patient data, and each data model conforming to at least one of the one or more schemas;
processing a search request against the index, the search request comprising one or more attribute of the abstract data type, wherein the search request is automatically expanded to retrieve one or more of the plurality of data models based on one or more additional attributes associated with the one or more attribute; and
providing a search result by collecting one or more shards based on the search request.

8. The system of claim 7, further comprising outputting a result of the search request.

9. The system of claim 8, wherein the output of the search request is sorted based on quality of match.

10. The system of claim 7, wherein populating the plurality of data models comprises generating and merging a data model for ingested patient data.

11. The system of claim 7, further comprising:
outputting the data models in a time series.

12. The system of claim 7, the abstract data type reflecting a class hierarchy.

13. A computer program product for modeling patient data, the computer program product comprising a computer readable storage medium having program instructions embodied therewith, the program instructions executable by a processor to cause the processor to perform a method comprising:
ingesting a collection of structured and unstructured patient data, the patient data comprising a plurality of modalities, the patient data comprising a longitudinal clinical history of one or more patients, the patient data from a plurality of data sources;
populating a plurality of data models based on the ingested patient data to provide for parallel search, retrieval, and hierarchical ranking of the patient data from the plurality of data sources, each data model comprising an abstract data type having a primary key configured to uniquely designate a row or a document, a search key configured to separately designate a row or a document, a grouping key configured to count number of matches to a query, and an untokenized key configured to preserve one or more predetermined fields of the document definition without tokenization, wherein the plurality of data models comprise one or more domain-specific subclasses;
storing the plurality of data models as one or more indexed documents in an index, each data model being associated with one or more schemas, each data model representing patient data according to one or more data types within the respective patient data, and each data model conforming to at least one of the one or more schemas;
processing a search request against the index, the search request comprising one or more attribute of the abstract data type, wherein the search request is automatically expanded to retrieve one or more of the plurality of data models based on one or more additional attributes associated with the one or more attribute; and
providing a search result by collecting one or more shards based on the search request.

14. The computer program product of claim 13, further comprising outputting a result of the search request.

15. The computer program product of claim 13, wherein populating the plurality of data models comprises generating and merging a data model for ingested patient data.

16. The computer program product of claim 13, further comprising:
outputting the data models in a time series.

17. The computer program product of claim 13, the abstract data type reflecting a class hierarchy.

* * * * *